United States Patent [19]

Lübbers et al.

[11] 4,255,053
[45] Mar. 10, 1981

[54] PHOTOMETER INCLUDING AUXILIARY INDICATOR MEANS

[75] Inventors: Dietrich W. Lübbers; Norbert Opitz, both of Dortmund, Fed. Rep. of Germany

[73] Assignee: Max-Planck-Gesellschaft zur Förderung der Wissenschaften e.V., Göttingen, Fed. Rep. of Germany

[21] Appl. No.: 903,411

[22] Filed: May 8, 1978

[30] Foreign Application Priority Data

May 6, 1977 [DE] Fed. Rep. of Germany ....... 2720370

[51] Int. Cl.³ ............................................. G01N 21/63
[52] U.S. Cl. ................................... 356/318; 356/417; 356/243; 422/83

[58] Field of Search ................ 356/39, 317, 318, 417, 356/243; 23/232 R; 422/83

[56] References Cited

U.S. PATENT DOCUMENTS 4,003,707   1/1977   Lubbers et al. ................... 356/39 X

*Primary Examiner*—F. L. Evans
*Attorney, Agent, or Firm*—Ladas & Parry

[57] ABSTRACT

An apparatus for an optical measurement of the concentration of substances including at least one monochromator means, one photometer means and one optometric means. A further reference indicator means is added to the indicator means. This further indicator means changes the measuring light and will not be changed by the concentration of the substance to be measured.

8 Claims, 2 Drawing Figures

PHOTOMETER INCLUDING AUXILIARY INDICATOR MEANS

BACKGROUND OF THE INVENTION

1. Field of the Invention

The present invention relates to an apparatus for investigating the concentration of a material by means of optodes.

2. Description of the Prior Art

The term "optode" is used hereinafter to denote an optometric device comprising wall means which define an indicator chamber, the wall means including at least one transparent wall portion, and the indicator chamber containing an indicator substance which is effective to modify the spectral characteristics of light incident thereon. It is known to use an optode to investigate the concentration of a material in a space containing the material. In this case, the wall means of the optode include a permeable wall portion, i.e. a wall portion through which the material under investigation can diffuse, and the optode is disposed with this permeable wall portion facing the space containing the material; and the indicator substance is selected so that the modification effected in the spectral characteristics of light incident thereon is dependent upon the concentration of the material under investigation in the indicator chamber.

The term "measuring indicator substance" or "measuring indicator" is used hereinafter to denote an indicator substance which is effective to modify the spectral characteristics of light incident thereon in a manner dependent upon the concentration of a material under investigation in the indicator chamber, and the term "measuring optode" is used hereinafter to denote an optode having a permeable wall portion and containing a measuring indicator substance.

Now, oftentimes the only measuring indicators are available are those which under influence of the material under investigation change only the intensity of the spectral distribution. In such case quantitative measurements are impossible if the concentration of the indicator, other optically caused changes of intensity or electronic changes, e.g. the amplification or gain do not enter definably into the resulting measurement values. Therefore, a large number of fluorescence-, absorption-, reflection-, and luminescence indicators cannot be utilized for such measurements. In particular, it is not possible by use of measuring microoptodes or nanooptodes, i.e. measuring optodes having a diameter less than 10 μm, which can be added to a carrier substance, to determine the concentration of the optodes or the relative concentration of the optodes.

SUMMARY OF THE INVENTION

Hence, it is a general object of the present invention to provide an improved construction of an apparatus for an optical measurement of the concentration of substances which overcomes the above drawback.

According to one aspect of the present invention there is provided an apparatus for investigating the concentration of a material, comprising a measuring optode, a light source for generating beams of monochromatic light and directing them onto the measuring indicator substance contained in the indicator chamber of the measuring optode, and photometric means for determining spectral characteristics of light emitted from the indicator chamber by way of the transparent wall portion of the optode, wherein the improvement comprises a reference indicator substance contained in the indicator chamber in addition to the measuring indicator substance, said reference indicator substance being effective to modify the spectral characteristics of light incident thereon in a manner which is independent of the concentration of the material under investigation in the indicator chamber.

According to another aspect of the present invention there is provided an apparatus for investigating the concentration of a material, comprising a measuring optode, a light source for generating beams of monochromatic light and directing them onto the measuring indicator substance contained in the indicator chamber of the measuring optode, and photometric means for determining spectral characteristics of light emitted from the indicator chamber of the measuring optode wherein the improvement comprises a second optode in which the indicator chamber contains a second indicator substance which is effective to modify the spectral characteristics of light incident thereon in a manner which is independent of the material under investigation, the second optode being positioned so that the light beams generated by the light source are directed onto the second indicator substance contained in the indicator chamber of the second optode and the photometric means receive light emitted from the indicator chamber of the second optode.

The term "reference indicator substance" is used hereinafter to denote an indicator substance which is effective to modify the spectral characteristics of light incident thereon in a manner independent of a material under investigation, and the term "reference optode" is used hereinafter to denote an optode in which the indicator substance is a reference indicator substance.

DETAILED DESCRIPTION OF THE PREFERRED EMBODIMENT

The present invention will be more fully understood by reference to the following detailed description and to the accompanying drawing in which.

Figure 1:
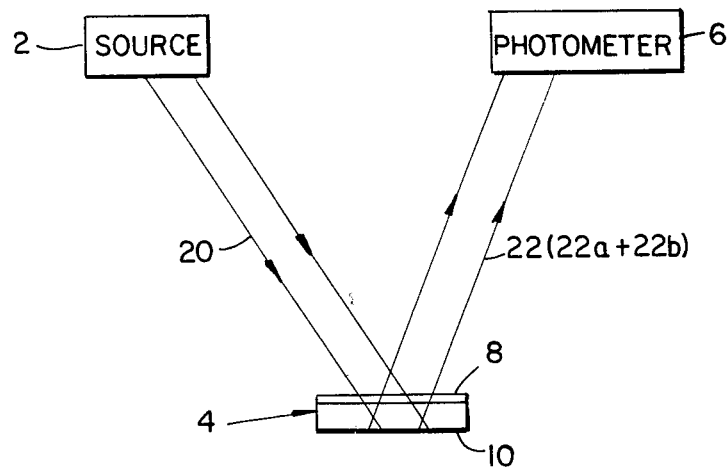
FIG. 1 illustrates diagrammatically an apparatus embodying the invention.

The apparatus illustrated in FIG. 1 comprises a light source 2, an optode 4 and a photometric device 6. The optode comprises a transparent member 8 and a membrane 10. The material under investigation is able to diffuse through the membrane 10 into an indicator chamber bounded by the member 8 and the membrane 10. The indicator chamber contains two indicator substances. One of the indicator substances is a measuring indicator substance which reacts to the presence of the material under investigation by emitting light having different spectral characteristics from light incident on the indicator substance, the difference in spectral chartertistics depending on the concentration of the material in the indicator chamber. The other indicator substance is a reference indicator substance which emits light having different spectral characteristics from light incident thereon, the difference in spectral characteristics being independent of the concentration of the material under investigation.

The source 2 emits a beam 20 of monochromatic light which is directed onto the indicator substances contained in the indicator chamber by way of the transparent member 8. The presence of the indicator substances in the indicator chamber causes a light beam 22 to be emitted through the transparent member 8 of the optode. The emitted light beam 22 includes one component 22a (a measuring component) having spectral characteristics different from the beam 20, the difference being dependent upon the concentration of the material under investigation in the indicator chamber, and another component 22b (a reference component) also having different spectral characteristics from the beam 20, the difference being independent of the concentration of the material under investigation in the indicator chamber. The photometric device 6 is positioned to receive the light beam 22 and generates two signals $M_1$ and $M_2$ representative of the intensity of light received at two measuring wavelengths $\lambda_1$ and $\lambda_2$ respectively.

Figure 2:
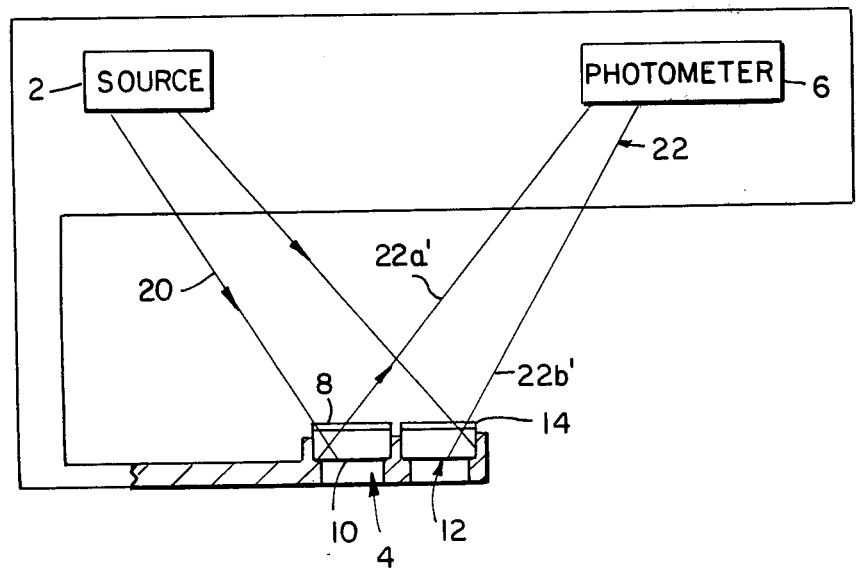
FIG. 2 illustrates a modification thereof.

In the modification illustrated in FIG. 2, the indicator chamber of the optode 4 does not contain the reference indicator substance, but there is provided instead a reference optode 12, having a transparent member 14 bounding an indicator chamber which contains the reference indicator substance. The light beam 20 from the source 2 impinges both upon the measuring optode 4 and upon the reference optode 12, and the light beam 22 received by the photometric device 6 from the optodes 4 and 12 includes a measuring component 22a' having spectral characteristics which are different from those of the light beam 20, the difference being dependent upon the concentration of the material under investigation in the indicator chamber of the optode 4, and a reference component 22b' having spectral characteristics which are different from those of the beam 20, the difference being independent of the concentration of material under investigation in the indicator chamber of the optode 12. As before, the photometric device generates two measuring signals $M_1$ and $M_2$, representative of the intensity of light received at two measuring wavelengths $\lambda_1$ and $\lambda_2$ respectively.

By using now such indicators which merely change the intensity of the spectral distribution and additionally for quantitative, calibrated measurements many advantages are achieved. This is true for indicators with exclusively absorption spectrums and for such with an exclusive change of intensity of the fluorescence, of the luminescence or of the reflection.

The present invention makes it possible to use microoptodes or nanooptodes in which the measuring indicator substance merely changes the intensity of the spectral distribution to determine the concentration of the optodes or the relative concentration of the optodes. This is done by use f a reference indicator substance. The reference indicator substance may be provided in the indicator chamber of the measuring optode, in addition to the measuring indicator substance, provided there is no mutual influence of the indicator substances respectively, or it may be provided in separate reference microoptodes or nanooptodes.

A specifically advantageous selection of a reference indicator is such that the reference indicator has no wavelength in common with the measuring indicator, i.e. there is no overlap between the spectra of light observed from the two indicator substances when illuminated by the same source. When the following equations are taken into consideration:

$$M_1 = S_1[J_1(\lambda_1), P]v(t) \quad (1)$$
$$M_2 = S_2[J_2(\lambda_2)]v(t)$$

where $M_1$, $M_2$ are the measuring signals obtained at the wavelengths $\lambda_1$, $\lambda_2$ respectively, the values $S_1$, $S_2$ the true signals at the wavelengths $\lambda_1$, $\lambda_2$; $J_1$ is the measuring indicator; $J_2$ is the reference indicator; v(t) the factor describing the distortion of the intensity, which can also be time dependent; and P the concentration of the substance to be measured; the following is applicable:

$$\frac{M_1}{M_2} = \frac{S_1[J_1(\lambda_1)P] \times v(t)}{S_2[J_2(\lambda_2)] \times v(t)} = \frac{S_1}{S_2} \quad (2)$$

Accordingly, if a quotient is formed, the distortions v(t) drop out. The quotient is free of distortions.

However, it is still possible to use further yet reference indicators which have wavelengths corresponding to the wavelengths of the measuring indicator. Thus, if the measuring signals are in form of:

$$M_1 = S_1[J_1(\lambda_1)_1P] \times v(t) + S_1'[J_2(\lambda_1)] \times v(t) \quad (3)$$
$$M_2 = S_2'[J_1(\lambda_2)_1P] \times v(t) + S_2[J_2(\lambda_2)] \times v(t)$$

where the additional true signals $S_1'(J_2, \lambda_1)$ (generated by reference indicator) and $S_2'(J_1, \lambda_2)$ (generated by measuring indicator), are those which arise due to overlapping, then—in case that the distortion v(t) is independent from all test conditions and conclusively, such as assumed in equation (1)–(3) mathematically separable—v(t) drops out, too, leading to the following equation:

$$\frac{M_1}{M_2} = \frac{S_1[J_1(\lambda_1),P] + S_1'[J_2(\lambda_1)]}{S_2'[J_1(\lambda_2),P] + S_2[J_2(\lambda_2)]} . \quad (4)$$

In case now the effect f(P) of the concentration P of the substance is mathematically separable, the following will result:

$$\frac{M_1}{M_2} = \frac{S_1 \times f(P) + S_1'}{S_2' \times f(P) + S_2} . \quad (5)$$

Equation (5) is the quotient of two linear functions in f(P), the constant $S_1$, $S_1'$, $S_2'$, $S_2$ of which is definable by separate measurements at each indicator at a known concentration P. In this manner a conversion nomogram can easily be produced based on equation (5). Of a greater practical importance is, however, a utilization of calibration curves $$\frac{M_1}{M_2} = F(P)$$

which can be experimentally produced for every indicator mixture.

A further development of the invention is the fact that the spectrum of the reference indicator is shiftable by third means arranged outside.

The advantage is that additive disturbing components can be eliminated in case the spectrum of the reference indicator is shiftable by outside means such as temperature, illumination or similar and the signal is formed of the shifted and unshifted signal. The interconnection between the concentration of the substance and the shift caused by said outer means will also be appropriately defined by means of a calibration curve.

Additive disturbing components can however also be eliminated by the agency of the multicomponent anaylsis according to WODICK and LUEBBERS (Natwiss. 59/362/197).

According to a further embodiment of the invention the concentration of the reference indicator is stepwise set up in various calibration ranges.

The advantage is, that now calibrated optometric means can be produced.

This is specifically advantageous in such cases where the indicators are sealed in foils, because such foils can be packed light- and gas-tight, such that calibration standards are produced with which the measuring devices for the optometric measuring procedure can be calibrated. Furthermore it is possible to define optimal ranges for the measurement.

A further advantage is achieved in case that several spatially separated areas of varying concentration are arranged on a foil, because in such case a fast finding of the optimal calibration range is possible.

While there are shown and described present preferred embodiments of the invention, it is to be distinctly understood that the invention is not limited thereto, but may be otherwise variously embodied and practiced within the scope of the following claims. Accordingly,

What is claimed is:

1. An apparatus for investigating the concentration of a material, comprising an optometric device which includes wall means defining an indicator chamber, said wall means including a transparent wall portion and a wall portion through which the material under investigation can diffuse and the indicator chamber containing a first indicator substance which reacts to the presence of said material under investigation by modifying the spectral characteristics of light incident thereon in a manner which depends on the concentration of said material in the indicator chamber, and the apparatus also comprising a light source for generating beams of monochromatic light and directing them onto the indicator substance contained in the indicator chamber by way of said transparent wall portion, and photometric means for determining spectral characteristics of light emitted from the indicator chamber by way of said transparent wall portion, wherein the improvement comprises a second indicator substance contained in the indicator chamber in addition to the first indicator substance and modifying the spectral characteristics of light incident thereon in a manner which is independent of the concentration of said material.

2. An apparatus for investigating the concentration of a material, comprising a first optometric device which includes wall means defining an indicator chamber, said wall means including a transparent wall portion and a wall portion through which the material under investigation can diffuse and the indicator chamber containing a first indicator substance which reacts to the presence of said material under investigation by modifying the spectral characteristics of light incident thereon in a manner which depends on the concentration of said material in the indicator chamber, and the apparatus also comprising a light source for generating beams of monochromatic light and directing them onto the indicator substance contained in the indicator chamber by way of said transparent wall portion, and photometric means for determining spectral characteristics of light emitted from the indicator chamber by way of said transparent wall portion, wherein the improvement comprises a second optometric device which incudes wall means defining a second indicator chamber, said wall means including a transparent wall portion and the second indicator chamber containing a second indicator substance which modifies the spectral characteristics of light incident thereon in a manner which is independent of the concentration of said material, and the improvement further comprising means positioning the second optometric device so that light of the beams generated by the light source is directed onto the second indicator substance contained in the second indicator chamber by way of said transparent wall portion of the second optometric device and the photometric means receive light emitted from the second indicator chamber by way of said transparent wall portion of the second optometric device.

3. An apparatus as claimed in claim 2, wherein said first and second optometric devices are micro-optometric devices.

4. An apparatus as claimed in claim 1 or 2, wherein there is no overlap between the spectral modification effected by the first indicator substance and that effected by the second indicator substance.

5. An apparatus as claimed in claim 1 or 2, wherein the spectral modification effected by the second indicator substance is shifable by external means.

6. An apparatus as claimed in claim 1 or 2, wherein the concentration of the second indicator substance is adjusted to various calibration ranges.

7. An apparatus as claimed in claim 1 or 2, wherein spatially separate areas on a common foil are provided with different respective concentrations of said second indicator substance.

8. An apparatus as claimed in claim 7, wherein said foil is packed in light-tight and gas-tight manner.

* * * * *